United States Patent
Kim

(10) Patent No.: US 10,162,938 B2
(45) Date of Patent: Dec. 25, 2018

(54) HEALTH MANAGEMENT SYSTEM USING HOME NETWORK AND OPERATION METHOD THEREOF

(71) Applicant: Samsung Electronics Co., Ltd., Gyeonggi-do (KR)

(72) Inventor: Young-Kyu Kim, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 210 days.

(21) Appl. No.: 13/778,028

(22) Filed: Feb. 26, 2013

(65) Prior Publication Data

US 2013/0238348 A1 Sep. 12, 2013

(30) Foreign Application Priority Data

Mar. 8, 2012 (KR) .......................... 10-2012-0024016

(51) Int. Cl.
| | | |
|---|---|---|
| *G16H 40/67* | (2018.01) | |
| *G16H 40/60* | (2018.01) | |
| *G06F 19/00* | (2018.01) | |
| *G16H 40/40* | (2018.01) | |

(52) U.S. Cl.
CPC ......... *G06F 19/3418* (2013.01); *G16H 40/40* (2018.01); *G16H 40/60* (2018.01); *G16H 40/67* (2018.01)

(58) Field of Classification Search
CPC .... G06F 19/3418; G16H 40/60; G16H 40/40; G16H 40/67
See application file for complete search history.

(56) References Cited

U.S. PATENT DOCUMENTS

| | | |
|---|---|---|
| 2002/0163534 A1 | 11/2002 | Choi et al. |
| 2003/0227439 A1* | 12/2003 | Lee .................... G06K 9/00221 345/156 |
| 2005/0119917 A1 | 6/2005 | Kim |
| 2005/0283532 A1 | 12/2005 | Kim et al. |
| 2006/0089727 A1 | 4/2006 | Drouet et al. |
| 2007/0057077 A1 | 3/2007 | Huang |
| 2009/0065596 A1* | 3/2009 | Seem et al. ..................... 236/51 |

(Continued)

FOREIGN PATENT DOCUMENTS

| | | |
|---|---|---|
| KR | 10-2002-0079203 | 10/2002 |
| KR | 10-0580661 B1 | 5/2006 |

(Continued)

OTHER PUBLICATIONS

International Search Report dated Jun. 24, 2013 in connection with International Patent Application No. PCT/KR2013/001294, 3 pages.

(Continued)

*Primary Examiner* — Christopher L Gilligan

(57) ABSTRACT

A health management system. A method of operating a home gateway for a home network connectable with at least one home device in the health management system includes receiving health information for at least one user from a health management server, generating environment control information for configuring an environment corresponding to the health information for the at least one user, and transmitting the environment control information to the at least one home device to control the at least one home device.

8 Claims, 11 Drawing Sheets

(56) References Cited

U.S. PATENT DOCUMENTS

| | | | |
|---|---|---|---|
| 2009/0259493 A1* | 10/2009 | Venon et al. | 705/3 |
| 2011/0167250 A1 | 7/2011 | Dicks et al. | |
| 2011/0208532 A1 | 8/2011 | Rahman et al. | |
| 2012/0261481 A1* | 10/2012 | Donlan | H05B 1/0275 237/12 |
| 2013/0024029 A1* | 1/2013 | Tran | A61B 5/7267 700/278 |

FOREIGN PATENT DOCUMENTS

| KR | 10-0651729 B1 | 12/2006 |
|---|---|---|
| KR | 10-2009-0106149 | 10/2009 |
| KR | 10-2010-0025769 | 3/2010 |
| KR | 10-2011-0126997 | 11/2011 |

OTHER PUBLICATIONS

Written Opinion of the International Searching Authority dated Jun. 24, 2013, regarding International Patent Application No. PCT/KR2013/001294, 6 pages.

KIPO, Notice of Preliminary Rejection for Application No. KR 10-2012-0024016, dated Jun. 27, 2018, 17 pages.

\* cited by examiner

HEALTH MANAGEMENT SYSTEM USING HOME NETWORK AND OPERATION METHOD THEREOF

CROSS-REFERENCE TO RELATED APPLICATION(S) AND CLAIM OF PRIORITY

The present application is related to and claims the benefit under 35 U.S.C. § 119(a) of a Korean patent application filed in the Korean Intellectual Property Office on Mar. 8, 2012 and assigned Serial No. 10-2012-0024016, the entire disclosure of which is hereby incorporated by reference.

TECHNICAL FIELD OF THE INVENTION

The present disclosure relates to a health management system. More particularly, the present disclosure relates to a system for providing a heath management service by using a home network and an operation method thereof.

BACKGROUND OF THE INVENTION

With the increasing use of portable terminals, various applications (hereinafter, simply referred to as "app") are provided. In particular, due to the growing concerns on health, apps for managing user's health have recently been provided. The apps for managing the user's health receive a heath condition directly from a user, and provide a result on the input health condition. For example, if the user reads, one-by-one, health check items provided by the health management app and checks off an item determined to coincide with the user's health condition, the health management app diagnoses the user's health condition on the basis of the item checked off by the user, and thereafter provides a diagnosis result to the user.

However, since the aforementioned method of determining the user's health condition is based on a self-test of the user, it is difficult to provide a correct diagnosis result based on the user's health condition. In addition, since the user confirms the diagnosis result by directly checking off the items in the conventional health management apps, it is difficult to attract users' interests, and thus there is a limitation in that the health management is just a one-off management instead of being persistently maintained.

SUMMARY OF THE INVENTION

To address the above-discussed deficiencies of the prior art, it is a primary object to provide a method and apparatus for a health management system using a home network.

Another aspect of the present disclosure is to provide a method and apparatus for configuring an environment according to user health information by receiving the user health information by a home gateway server from a health management server in a health management system using a home network.

Another aspect of the present disclosure is to provide a method and apparatus for providing an environment suitable for a user's health condition by using a home device in a health management system using a home network.

Another aspect of the present disclosure is to provide a method and apparatus for providing user's health information by using a plurality of portable terminals registered to a home network in a health management system using the home network.

In accordance with an aspect of the present disclosure, a method of providing, a health management service in a home gateway server for a home network connectable with at least one home device is provided. The method includes receiving health information for at least one user from a health management server, generating environment control information for configuring an environment corresponding to the health information for the at least one user, and transmitting the environment control information to the at least one home device to control the at least one home device, wherein the environment corresponding to the health information for the at least one user can be configured by controlling the at least one home device on the basis of the environment control information.

In accordance with another aspect of the present disclosure, a method of providing a health management service in a health management server is provided. The method includes storing health information for each of a plurality users, detecting a health information transmission event for at least one user, searching health information for the at least one user from pre-stored health information for the plurality of users, and transmitting the found health information for the at least one user to a home gateway server.

In accordance with another aspect of the present disclosure, a method of providing a health management service in a home device connectable to a home network is provided. The method includes receiving first environment control information for configuring an environment from a home gateway server, receiving second environment control information for configuring an environment from a user, and configuring an environment corresponding to any one of the first environment control information and the second environment control information according to a priority of the first environment control information and the second environment control information.

In accordance with another aspect of the present disclosure, a method of providing a health management service in a portable terminal connectable to a home network is provided. The method includes receiving health information for at least one user from a home gateway server, and displaying the received health information for the at least one user, wherein the health information is health information for at least one user registered to the home gateway server.

In accordance with another aspect of the present disclosure, an apparatus for providing a health management service in a home gateway server for a home network connectable with at least one home device is provided. The apparatus includes a communication unit for receiving health information for at least one user from a health management server, and for transmitting environment control information for configuring an environment corresponding to the received health information to the at least one home device, and a controller for generating the environment control information corresponding to health information for the at least one user to control the at least one home device, wherein the environment corresponding to the health information for the at least one user can be configured by controlling the at least one home device on the basis of the environment control information.

In accordance with another aspect of the present disclosure, an apparatus for providing a health management service in a health management server is provided. The apparatus includes a memory for storing health information for each of a plurality users, a controller for detecting a health information transmission event for at least one user, and for searching health information for the at least one user from health information for the plurality of users and pre-stored in the memory, and a communication unit for transmitting the found health information for the at least one user to a home gateway server.

In accordance with another aspect of the present disclosure, an apparatus for providing a health management service in a home device connectable to a home network is provided. The apparatus includes a communication unit for receiving first environment control information for configuring an environment from a home gateway server, an input unit for receiving second environment control information for configuring an environment from a user, and a controller for configuring an environment corresponding to any one of the first environment control information and the second environment control information according to a priority of the first environment control information and the second environment control information.

In accordance with another aspect of the present disclosure, an apparatus for providing a health management service in a portable terminal connectable to a home network is provided. The apparatus includes a communication unit for receiving health information for at least one user from a home gateway server and a health management server, a controller for controlling a function for displaying the health information for the at least one user, and a display unit for displaying the health information under the control of the controller, wherein the health information is health information for at least one user registered to the home gateway server.

Before undertaking the DETAILED DESCRIPTION OF THE INVENTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE INVENTION

FIGS. 1 through 11, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device. Exemplary embodiments of the present disclosure will be described herein below with reference to the accompanying drawings. In the following description, well-known functions or constructions are not described in detail since they would obscure the invention in unnecessary detail. Also, the terms used herein are defined according to the functions of the present invention. Thus, the terms may vary depending on a user's or operator's intension and usage. That is, the terms used herein must be understood based on the descriptions made herein.

The present disclosure described below relates to a method and apparatus for a health management system using a home network.

Figure 1:
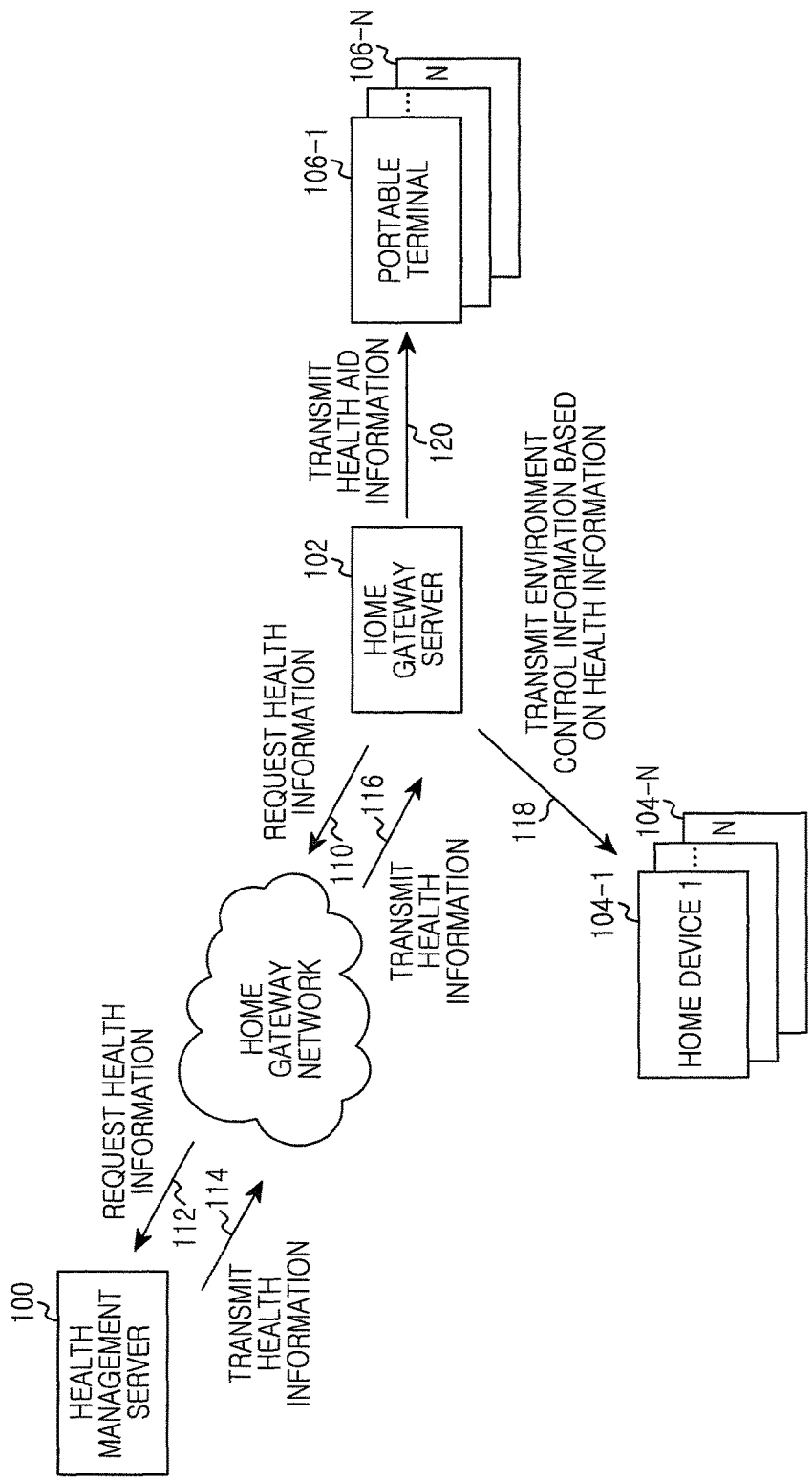
FIG. 1 illustrates a structure of a health management system using a home network according to an exemplary embodiment of the present disclosure.

FIG. 1 illustrates a structure of a health management system using a home network according to an exemplary embodiment of the present disclosure.

Referring to FIG. 1, the health management system using the home network includes a health management server 100, a home gateway server 102, a plurality of home devices 104-1 to 104-N, and a plurality of portable terminals 106-1 to 106-N. Hereinafter, the plurality of home devices 104-1 to 104-N of the present disclosure may include indoor electronic devices related to user's everyday life and outdoor electronic devices. Examples of the indoor electronic device include a temperature controller, a humidity controller, an illumination controller, an air cleaner, etc. Examples of the outdoor electronic device include a vehicle controller, a vehicle navigation, and an electronic device used outside an office, or the like. In addition, the health management server 100 is a server for storing and managing health information of the user by collecting the health information, and may be a hospital server or a specific server.

The health management server 100 stores and manages users' health information acquired by a medial specialist through a physical examination. According to the present disclosure, the health management server 100 receives a health information request signal from the home gateway server 102 and provides per-user health information. Herein, the health information may include a physical examination record of the user, prescription information, treatment reservation information, and related medical information. In step 110 and step 112, the health management server 100 receives the user's health information request signal from the home gateway server 120 via a home gateway network. Upon receiving the user's health information request signal, the health management server 100 searches health information of a corresponding user from pre-stored per-user health information. Thereafter, in step 114 and step 116, the health management server 100 transmits the found user's health information to the home gateway server 102 via the home gateway network. For example, upon receiving a signal for requesting health information of a user 1 from the home gateway server 102, the health management server 100 searches the health information of the user 1 from the plurality of pieces of user health information, and thereafter transmits the found health information of the user 1 to the home gateway server 102.

The home gateway server 102 analyzes the user health information received from the health management server 100 and generates environment control information and health aid information. According to the present disclosure, the environment control information implies information for controlling a user environment, such as a temperature, a humidity, an illumination, an air cleanness, a diet, etc. The health aid information may be medical information related to user's health such as a user's illness or disease name, a cause, a symptom, a prescription, a health condition, a cure and prevention, treatment reservation information, and food. In step 118, the home gateway server 102 transmits the generated environment control information to at least one or more home devices 104-1 to 104-N. In addition, in step 120, the home gateway server 102 transmits the generated health aid information to at least one of the portable terminals 106-1 to 106-N. For example, the home gateway server 102 analyzes the user health information received from the health management server 100, and generates the environment control information and the health aid information. Thereafter, the home gateway server 102 transmits temperature information included in the generated environment control information to a temperature controller, transmits humidity information to a humidity controller, and transmits the health aid information to at least one of the portable terminals 106-1 to 106-N.

Upon receiving the environment control information from the home gateway server 102, the plurality of home devices 104-1 to 104-N control an environment according to the received environment control information. In particular, each of the home devices 104-1 to 104-N may receive different environment control information for each user. For example, the home device-1 104-1 of the user 1 controls the environment by receiving environment control information of the user 1, and the home device-2 104-2 of the user 2 controls the environment by receiving environment control information of the user 2.

In step 120, the plurality of portable terminals 106-1 to 106-N may receive the health aid information of the user from the home gateway server 102 and may display the received information. In this example, the health aid information may be health aid information for users of the portable terminals 106-1 to 106-N or health aid information for other family members. In addition, the portable terminals 106-1 to 106-N may receive a query related to health from the user, and may transmit the received query to the home gateway server 102.

Figure 2:
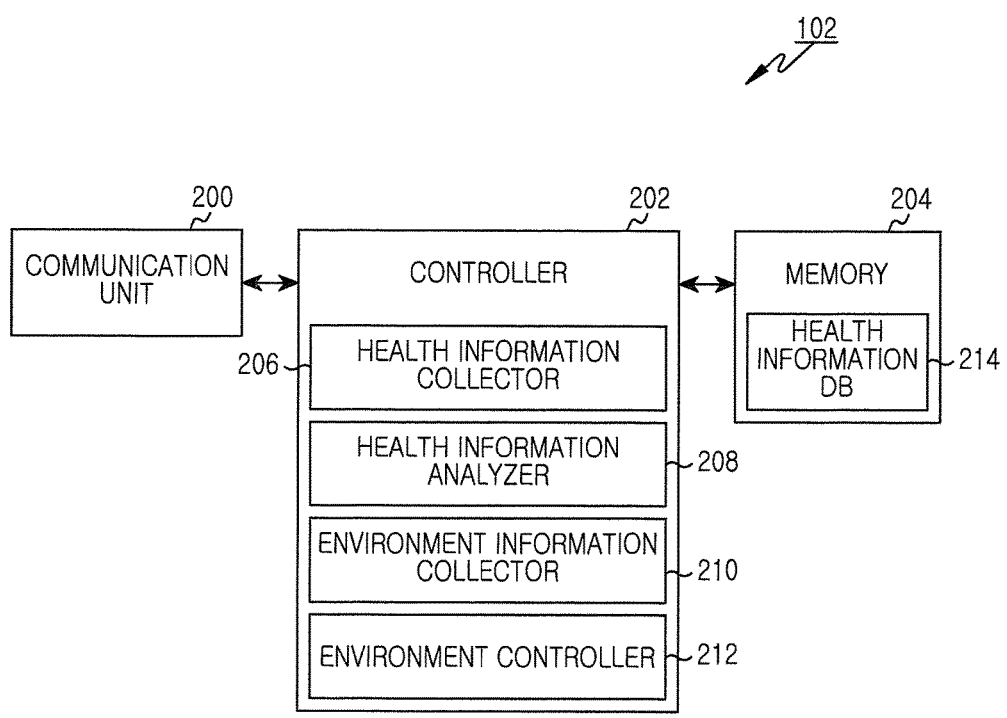
FIG. 2 illustrates a block diagram of a home gateway server according to an exemplary embodiment of the present disclosure.

FIG. 2 illustrates a block diagram of the home gateway server 102 according to an exemplary embodiment of the present disclosure.

Referring to FIG. 2, the home gateway server 102 includes a communication unit 200, a controller 202, and a memory 204. In addition, the controller 202 may include a health information collector 206, a health information analyzer 208, an environment information collector 210, and an environment controller 212. The memory 204 may include a health information. DataBase (DB) 214.

First, the communication unit 200 performs a function for transmitting and receiving a signal under the control of the controller 202. That is, the communication unit 200 transmits a user health information request signal to the health management server 100 under the control of the controller 202, and receives a health information signal for indicating a health condition of the user from the health management server 100. Further, the communication unit 200 transmits to the plurality of home devices 104-1 to 104-N registered to the home gateway server 102 the environment control information received from the controller 202, and transmits to at least one of the portable terminals 106-1 to 106-N the user health aid information received from the controller 202.

The controller 202 controls and processes an overall operation of the home gateway server 102. In particular, upon receiving the user health information from the health management server 100, the controller 202 generates the environment control information and the health aid information according to the received user health information. Herein, on the basis of the per-user health information received from the health management server 100, the health aid information may be generated by using a search operation of an external server or the health information DB 214 included in the home gateway server 102.

The health information collector 206 included in the controller 202 performs a function for collecting health information of users registered to the home gateway server 102 in every pre-set period from the health management server 100.

The health information analyzer 208 analyzes the per-user health information collected by the health information collector 206, generates essential environment information and health aid information corresponding to the per-user health information, and thereafter stores the essential environment information and the health aid information to the memory 204. In this example, the essential environment information implies an environment required according to a current health condition of each user as a result of analyzing the per-user health information, and may be information such as a temperature, a humidity, an illumination, an air cleanness, a diet, etc., which is necessary for the user.

The environment information collector 210 collects environment information for a user's living environment. In particular, for each user, the environment information collector 210 collects current environment information regarding a location of a place where the user spends most of the time. For example, the environment information collector 210 may collect current environment information of a main room and a kitchen where a user 1 spends most of the time. In this example, the current environment information may be information such as a temperature, humidity, illumination, air cleanness, etc., of the main room and the kitchen at the moment. Further, the environment information collector 210 may collect current environment information of a secondary room and a veranda where a user 2 spends most of the time. Herein, locations of places where users spend most of the times can be determined by using location information of the portable terminals 106-1 to 106-N used by the respective users.

On the basis of the essential environment information generated by the health information analyzer 208 and the current environment information collected by the environment information collector 210, the environment controller 212 generates environment control information required by the home devices 104-1 to 104-N to control the environment. That is, the environment controller 212 determines information for configuring an environment required for a current health condition of the user by using the essential environment information and the current environment information, and performs a function for managing the determined information for each of the home devices 104-1 to 104-N. For example, the environment controller 212 generates temperature control information for setting a temperature required for the user health condition on the basis of the essential temperature information and the current temperature information, and performs a control function for transmitting the generated temperature control information to a temperature controller. Further, the environment controller 212 performs a control function for delivering per-user environment control information to the home devices 104-1 to 104-N.

If the specific home device 104-N is a device commonly used by a plurality of users, and different pieces of environment control information are generated for the plurality of users, then the controller 202 may transmit to the specific home device 104-N only environment control information for a user having a high priority among the respective pieces of environment control information for the plurality of users. Herein, the priority may be determined and modified through an additional user input.

The memory 204 stores a variety of data and programs required for an operation of the home gateway server 102. The health information DB 214 stores health information, essential environment information, health aid information, current environment information, and environment control information provided from the controller 202. The stored health information, the essential environment information, the health aid information, the current environment information, and the environment control information may be provided to the controller 202 under the control of the controller 202 in a next environment control process. Further, the health information DB 214 may store essential environment information per health condition, and may store health-related medical information such as an illness or disease name, a cause, a symptom, a prescription, a health condition, a cure and prevention, treatment reservation information, and food in accordance with health information.

The method described above in relation with FIG. 2 under of the present invention may be provided as one or more instructions in one or more software modules stored in the respective home gateway server.

Figure 3:
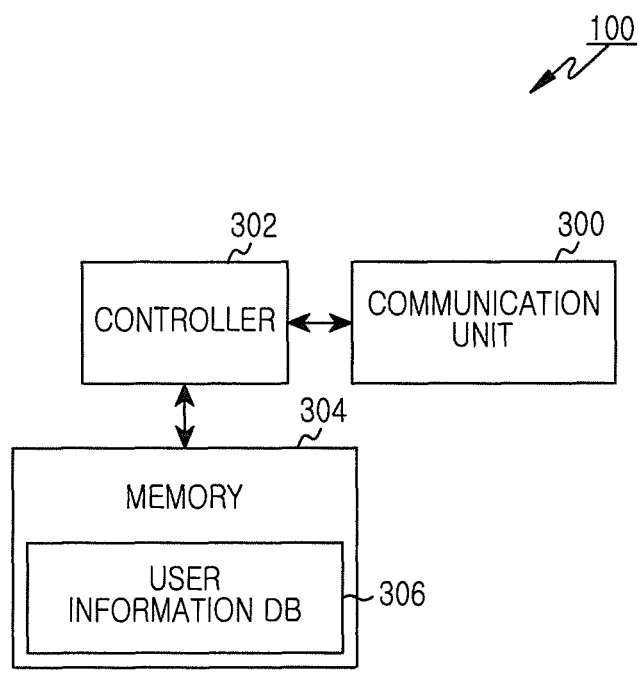
FIG. 3 illustrates a block diagram of a health management server according to an exemplary embodiment of the present disclosure.

FIG. 3 illustrates a block diagram of the health management server 100 according to an exemplary embodiment of the present disclosure.

Referring to FIG. 3, the health management server 100 includes a communication unit 300, a controller 302, and a memory 304. The memory 304 may include a user information DB 306.

The communication unit 300 performs a function for transmitting and receiving a signal under the control of the controller 302. In particular, the communication unit 300 receives a user health information request signal from the home gateway server 102, and transmits user health information to the home gateway server 102. Herein, the user health information request signal may include health information request signals for a plurality of users.

The controller 302 controls and processes an overall operation of the health management server 100. In particular, the controller 302 performs a function for acquiring and transmitting health information of a corresponding user in accordance with the user health information request signal. Specifically, upon receiving a signal for requesting health information of a specific user from the home gateway server 102, the controller 302 acquires the health information of the specific user from the memory 304 and performs a function for transmitting the health information to the home gateway server 102.

The memory 304 stores a variety of data and programs required for an operation of the health management server 100. The memory 304 includes the user information DB 306. The user information DB 306 may store a diagnosis record, prescription information, treatment reservation information, and related medical information for each of the plurality of users.

The method described above in relation with FIG. 3 under of the present invention may be provided as one or more instructions in one or more software modules stored in the respective health management server.

Figure 4:
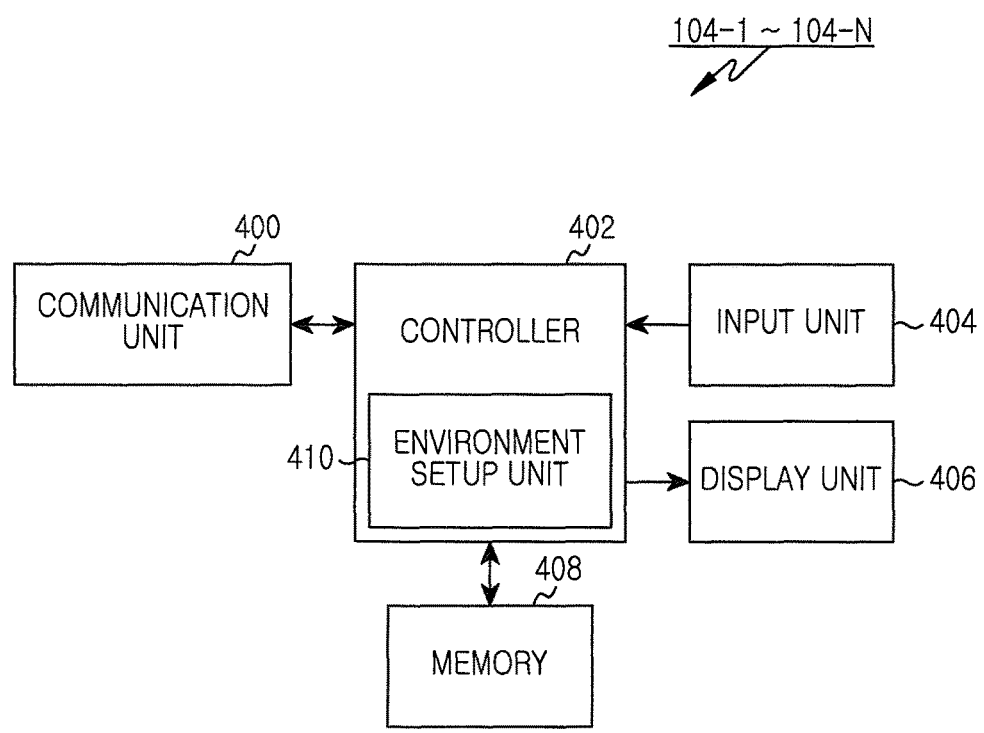
FIG. 4 illustrates a block diagram of a home device supporting a home network according to an exemplary embodiment of the present disclosure.

FIG. 4 illustrates a block diagram of the home devices 104-1 to 104-N supporting a home network according to an exemplary embodiment of the present disclosure.

Referring to FIG. 4, the home devices 104-1 to 104-N include a communication unit 400, a controller 402, an input unit 404, a display unit 406, and a memory 408. The controller 402 may include an environment setup unit 410.

The communication unit 400 transmits and receives a signal under the control of the controller 402. In particular, the communication unit 400 performs a function for receiving environment control information from the home gateway server 102 under the control of the controller 402.

The controller 402 controls and processes an overall operation of the home device, and controls the environment setup unit 410 according to the received environment control information and an additional user input signal. Specifically, upon receiving the environment control information from the home gateway server 102, the environment setup unit 410 configures an environment according to the received environment control information or configures the environment according to environment control information which is input from the user. If the environment control information is input from the user in a state in which the environment control information is received from the home gateway server 102, or if the environment control information is received from the home gateway server 102 in a state in which the environment control information is input from the user, the environment setup unit 410 may configure an environment corresponding to any one of the environment control information received from the home gateway server 102 and the environment control information input from the user according to a pre-set priority, or may configure the environment according to a priority which is input by the user.

The input unit 404 includes at least one function key and a touch sensor, receives environment control information by key pressing or touching of the user, and provides the input environment control information to the controller 402. For example, the input unit 404 may receive temperature control information from the user and provide the information to the controller 402.

The display unit 406 displays at least one of various state information, texts, and images generated during the operation of the home devices 104-1 to 104-N. For example, the display unit 406 may display information for indicating a current state of an environment controlled by the home devices 104-1 to 104-N, such as a temperature, a humidity, an air cleanness, etc.

The memory 408 stores various programs and data required for the operation of the home devices 104-1 to 104-N. According to the present disclosure, the memory 408 may store control information including an environment setup history and an environment control history.

The method described above in relation with FIG. 4 under of the present invention may be provided as one or more instructions in one or more software modules stored in the respective home devices.

Figure 5:
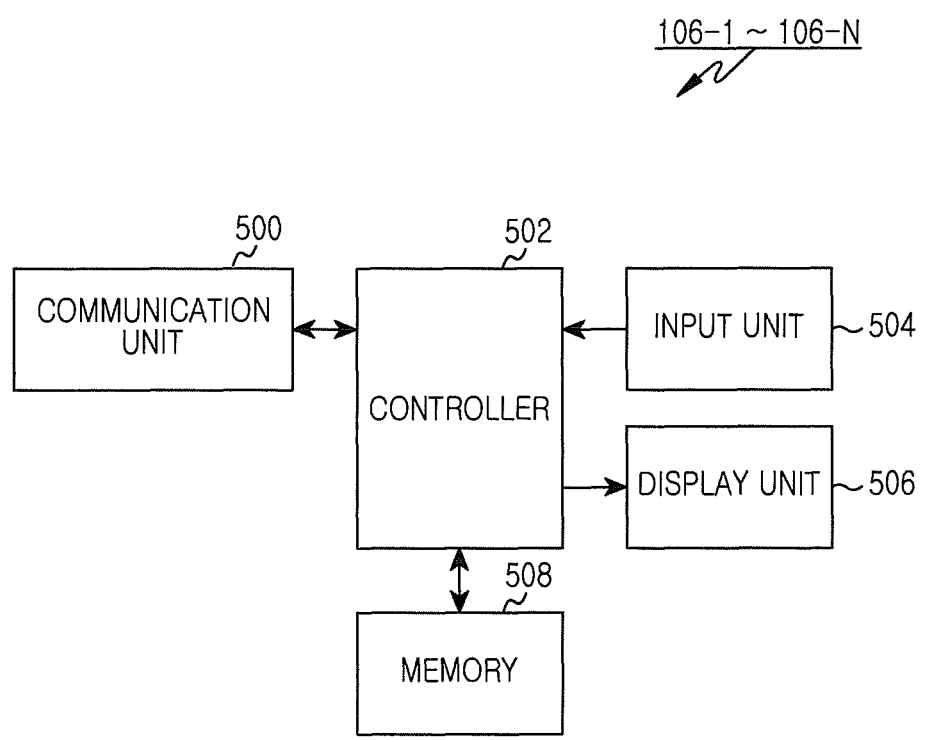
FIG. 5 illustrates a block diagram of a portable terminal supporting a home network according to an exemplary embodiment of the present disclosure.

FIG. 5 illustrates a block diagram of the portable terminals 106-1 to 106-N supporting a home network according to an exemplary embodiment of the present disclosure. The portable terminal may be an electronic device such as, for example, a laptop, a smart phone, a net book, a mobile internet device, an ultra mobile PC, a tablet personal computer, a mobile telecommunication terminal, PDA having a camera and the like herein, just to name some of the possibilities.

Referring to FIG. 5, the portable terminals 106-1 to 106-N include a communication unit 500, a controller 502, an input unit 504, a display unit 506, and a memory 508.

The communication unit 500 transmits and receives a signal under the control of the controller 502. Specifically, the communication unit 500 performs a function for receiving health aid information for users of the portable terminals 106-1 to 106-N or other users from the home gateway server 102, and may transmit a signal including a user query which is input under the control of the controller 502.

The controller 502 controls and processes an overall operation of the portable terminals 106-1 to 106-N. In particular, the controller 502 controls and processes a function for providing health aid information for the users of the portable terminals 106-1 to 106-N or other users. In addition, the controller 502 receives user input information from the input unit 504, and controls and processes a transmission function.

The input unit 504 includes at least one function key and a touch sensor, and provides the controller 502 with input information which is input by the user. The input information may include a user's query and a variety of information regarding user's health.

The display unit 506 displays at least one of a variety of state information, texts, and images generated during the operation of the portable terminals 106-1 to 106-N, and performs a function for displaying health aid information of the user. Herein, the health aid information of the user may be health aid information for the users of the portable terminals 106-1 to 106-N or other users.

The memory 508 stores various programs and data required for the operation of the portable terminals 106-1 to 106-N. In particular, the memory 508 may store health aid information of the user, and may store user input information under the control of the controller 502.

The method described above in relation with FIG. 5 under of the present invention may be provided as one or more instructions in one or more software modules stored in the respective portable terminals.

Figure 6:
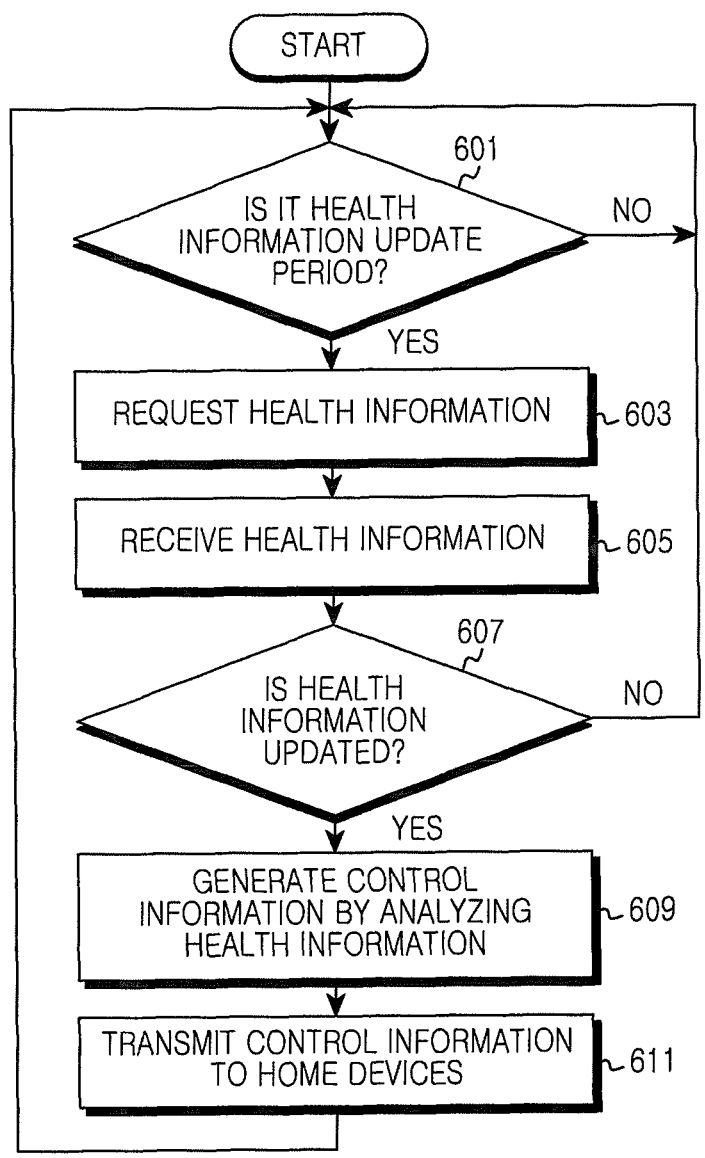
FIG. 6 illustrates a process of operating a home gateway server according to an exemplary embodiment of the present disclosure.

FIG. 6 illustrates a process of operating the home gateway server 102 according to an exemplary embodiment of the present disclosure.

Referring to FIG. 6, the home gateway server 102 examines whether it is a user's health information update period in step 601. The health information update period may be pre-set, and may be modified according to a user control. If it is the user's health information update period, proceeding to step 603, the home gateway server 102 transmits to the health management server 100 a signal for requesting health information on at least one user registered to the home gateway server 102. In step 605, the home gateway server 102 receives health information on the at least one user from the health management server 100. In step 607, the home gateway server 102 determines whether per-user health information is updated. That is, the home gateway server 102 examines whether per-user health information received from the health management server 100 is equal to per-user health information received in a previous update period.

If the received per-user health information is equal to the per-user health information received in the previous update period, returning to step 601, the home gateway server 102 stands by until a next health information update period comes. Otherwise, if the received per-user health information is different from the per-user health information received in the previous update period, the home gateway server 102 determines that the user's health information is updated. In step 609, the home gateway server 102 analyzes the per-user health information and generates environment control information and health aid information. In this example, the environment control information is generated by using essential environment information and current environment information on the basis of each user's health information. In addition, on the basis of the per-user health information received from the health management server 100, the health aid information may be generated by using a search operation of an external server or the health information DB 214 included in the home gateway server 102.

In step 611, the home gateway server 102 transmits the environment control information based on the per-user health information to the home devices 104-1 to 104-N, and transmits the health aid information based on the per-user health information to the plurality of portable terminals 106-1 to 106-N registered to the home network. In this example, the home gateway server 102 may determine the home devices 104-1 to 104-N corresponding to the respective users on the basis of locations of places where the users spend most of the time, and may generate different environment control information for each of the home devices 104-1 to 104-N according to the respective users of the home devices 104-1 to 104-N. For example, the home gateway server 102 may confirm that a user 1 spends most of the time in a main room and thus determine a temperature controller of the main room as the home device 104-1 of the user 1. Thereafter, according to a health condition of the user 1, the home gateway server 102 may generate environment control information for increasing a temperature of the main room by 3 degrees Celsius and may transmit the information to the temperature controller of the main room. Further, the home gateway server 102 may confirm that a user 2 spends most of the time in a secondary room and thus determine a temperature controller of the secondary room as the home device 104-2 of the user 2. Thereafter, according to a health condition of the user 2, the home gateway server 102 may generate environment control information for increasing a temperature of the secondary room by 5 degrees Celsius and may transmit the information to the temperature controller of the secondary room.

Thereafter, returning to step 601, the home gateway server 102 repeats the subsequent steps.

Figure 7:
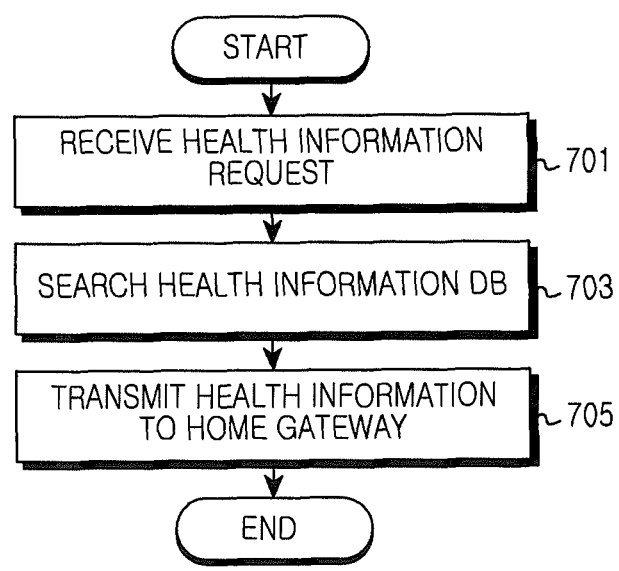
FIG. 7 illustrates a process of operating a health management server in a health management system using a home network according to an exemplary embodiment of the present disclosure.

FIG. 7 illustrates a process of operating the health management server 100 in a health management system using a home network according to an exemplary embodiment of the present disclosure.

Referring to FIG. 7, in step 701, the health management server 100 receives a signal for requesting health information on at least one user from the home gateway server 102. In step 703, the health management server 100 searches the requested health information on the at least one user from the user information DB 306 included in the health management server 100. In step 705, the health management server 100 transmits the health information to the home gateway server 102. The health information may include a diagnosis record, prescription information, treatment reservation information, and related medical information of a corresponding user. For example, upon receiving a signal for requesting health information on a user 1 from the specific home gateway server 102, the health management server 100 searches the health information on the user 1 from the user information DB 306 included in the health management server 100, and transmits the found health information on the user 1 to the home gateway server 102.

Thereafter, the health management server 100 ends the procedure of FIG. 7 according to the exemplary embodiment of the present disclosure.

Figure 8:
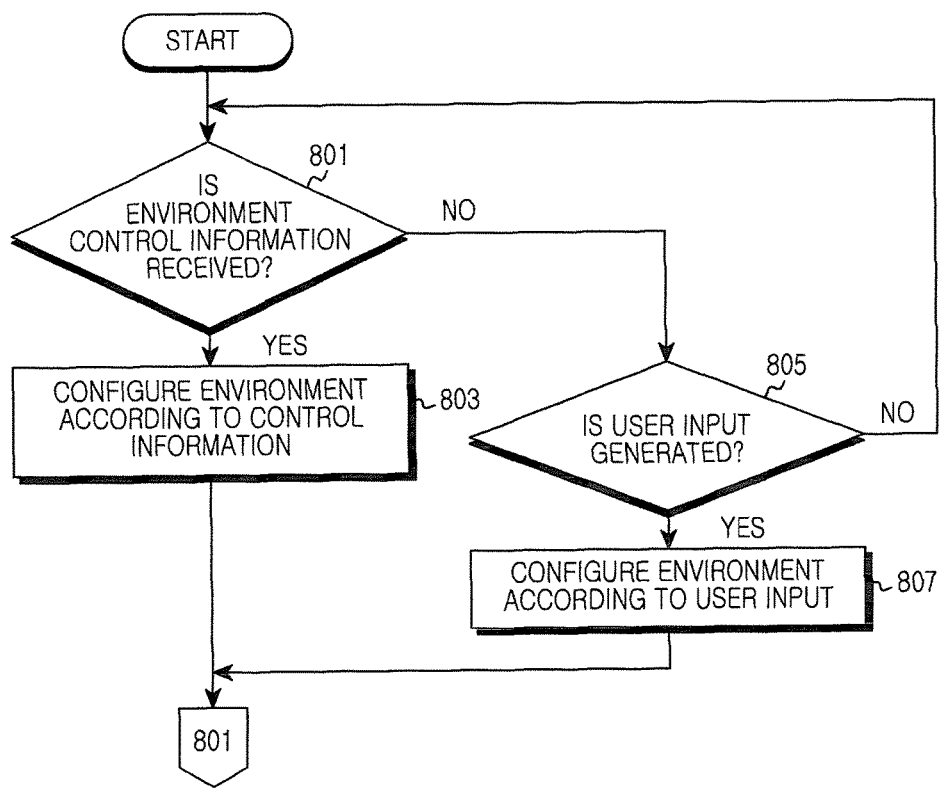
FIG. 8 illustrates a process of operating a home device in a health management system using a home network according to an exemplary embodiment of the present disclosure.

FIG. 8 illustrates a process of operating the home devices 104-1 to 104-N in a health management system using a home network according to an exemplary embodiment of the present disclosure.

Referring to FIG. 8, in step 801, the home devices 104-1 to 104-N examine whether environment control information is received from the home gateway server 102. If the environment control information is received from the home gateway server 102, the home devices 104-1 to 104-N configure an environment according to the received environment control information. For example, if the home devices 104-1 to 104-N are temperature controllers, the home devices 104-1 to 104-N receive temperature control information from the home gateway server 102, determine a temperature according to the received temperature control information, and thus can perform a heating or air-conditioning function.

If the environment control information is not received from the home gateway server 102 in step 801, proceeding to step 805, the home devices 104-1 to 104-N examine whether an input signal is received from a user. If the input signal is received from the user, proceeding to step 807, the home devices 104-1 to 104-N configure an environment according to the input signal received from the user. Otherwise, if the input signal is not received from the user, returning to step 801, the home devices 104-1 to 104-N repeat the subsequent steps. For example, if temperature control information is input from the user in a state in which the temperature control information is not received from the home gateway server 102, the temperature controller performs a temperature control according to the temperature control information input from the user.

Although not illustrated, if a user input signal for an environment configuration is received in a situation in which an operation is running by configuring an environment according to the environment control information received from the home gateway server 102, the home devices 104-1 to 104-N display a message for indicating that the environment is currently being configured according to the environment control information received from the home gateway server 102, and thus may allow the user to select whether to reconfigure the environment.

Figure 9:
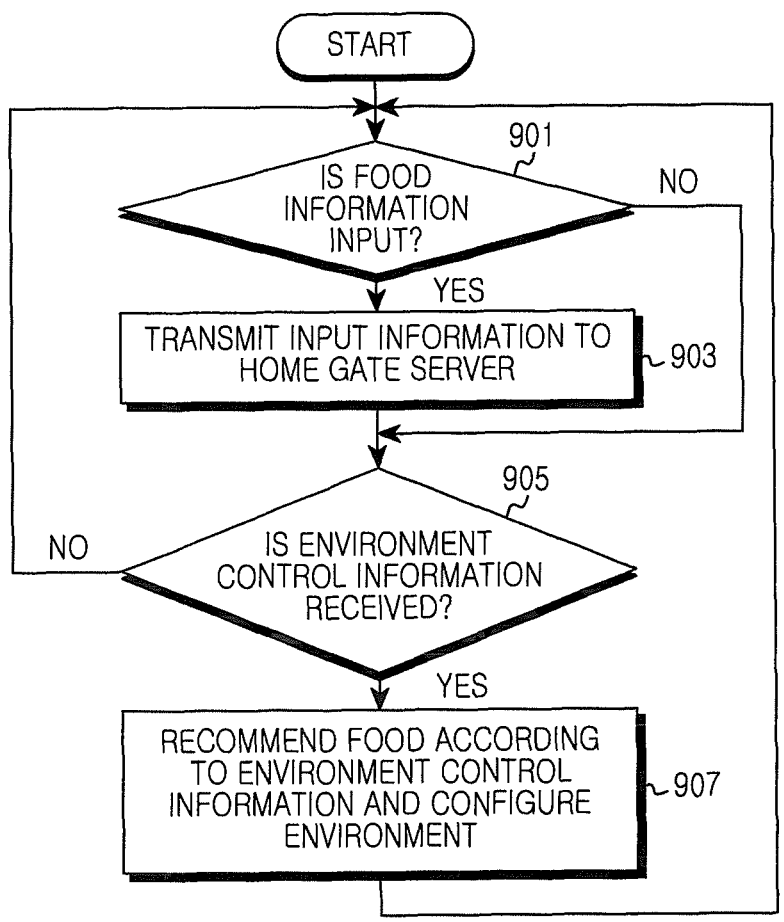
FIG. 9 illustrates a process of operating a refrigerator which is one of home devices in a health management system using a home network according to another exemplary embodiment of the present disclosure.

FIG. 9 illustrates a process of operating a refrigerator which is one of the home devices 106-1 to 106-N in a health management system using a home network according to another exemplary embodiment of the present disclosure.

Referring to FIG. 9, in step 901, the refrigerator examines whether information on food contained in the refrigerator is input from a user. If the food information is not input, the procedure directly proceeds to step 905. Otherwise, if the food information is input, proceeding to step 903, the refrigerator transmits the input food information to the home gateway server 102.

In step 905, the refrigerator examines whether environment control information is received from the home gateway server 102. If the environment control information is not received from the home gateway server 102, returning to step 901, the refrigerator repeats the subsequent steps. Otherwise, if the environment control information is received from the home gateway server 102, proceeding to step 907, the refrigerator configures an environment corresponding to the received environment control information. In this example, the environment control information of the refrigerator includes at least one of temperature control information and recommended restaurant information. Therefore, the refrigerator can control a temperature according to the received environment control information, and can acquire the recommended restaurant information from the received environment control information and then display the information on a screen.

Figure 10:
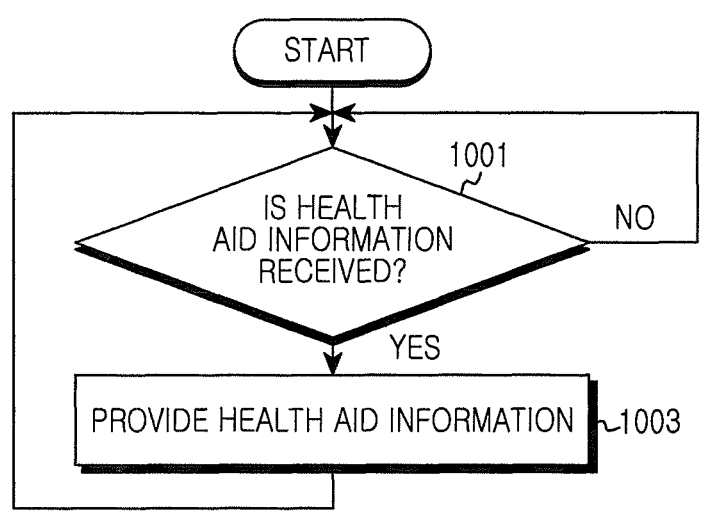
FIG. 10 illustrates a process of operating a portable terminal in a health management system using a home network according to an exemplary embodiment of the present disclosure.

FIG. 10 illustrates a process of operating the portable terminals 106-1 to 106-N in a health management system using a home network according to an exemplary embodiment of the present disclosure.

Referring to FIG. 10, the portable terminals 106-1 to 106-N examine whether health aid information is received from the home gateway server 102 in step 1001. Herein, the health aid information may be health aid information for the users of the portable terminals 106-1 to 106-N or health aid information for other users. Upon receiving the health aid information for the users of the portable terminals 106-1 to 106-N or other users from the home gateway server 102, proceeding to step 1003, the portable terminals 106-1 to 106-N display the health aid information on a screen and provide the information to the user. Although not illustrated, the portable terminals 106-1 to 106-N may receive a query on the health and a variety of input information related to the health of the user, such as user health state information, from the user, and may transmit the received information to the home gateway server 102 and the health management server 100. In this example, the portable terminals 106-1 to 106-N may communicate with the health management server 100 via the home gateway server 102, and may directly communicate with the health management server 100.

Figure 11:
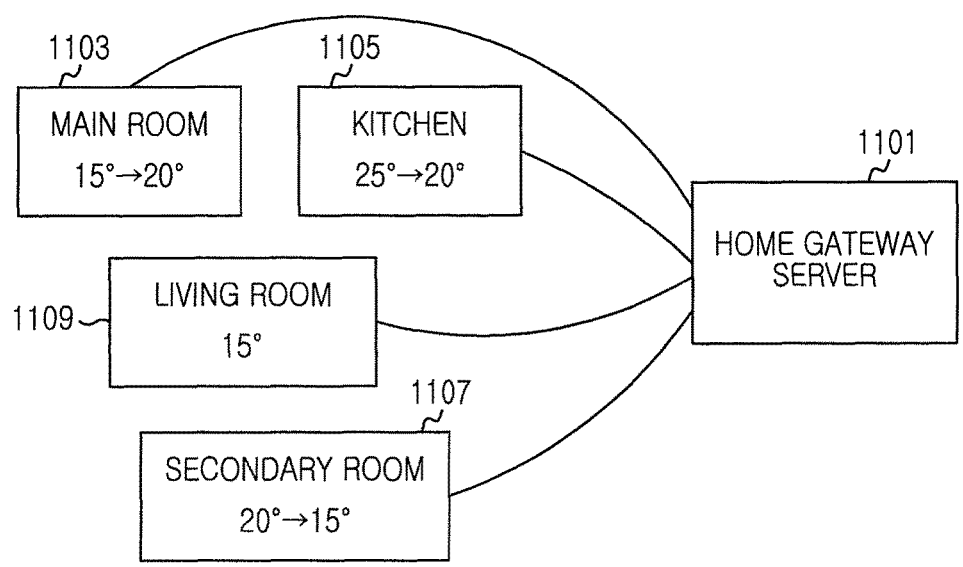
FIG. 11 illustrates a per-user environment configuration in a home gateway server according to an exemplary embodiment of the present disclosure.

FIG. 11 illustrates a per-user environment configuration in a home gateway server 1101 according to an exemplary embodiment of the present disclosure.

Referring to FIG. 11, the home gateway server 1101 acquires per-user health information from the health management server 100, and generates and transmits environment control information for each of home devices 104-1 to 104-N according to the per-user health information. Thus, the home gateway server 1101 can configure an environment for each user. For example, upon receiving health information of a user 1 and a user 2 from the health management server 100, the home gateway server 1101 may analyze the health information of the user 1 and then determine that a room temperature of 20 degrees Celsius is required as the environment for the user 1, and thereafter may perform a function for controlling a temperature of a main room 1103 and a kitchen 1105, in which the user 1 spends most of the time, to 20 degrees Celsius. Further, the home gateway server 1101 may analyze health information of the user 2 and then determine that a room temperature of 15 degrees Celsius is required as an environment for the user 2, and thereafter may perform a function for controlling a temperature of a secondary room 1107 and a living room 1109, in which the user 2 spends most of the time, to 15 degree Celsius.

Although it is described above that the home gateway server 102 requests user health information to the health management server 100 with a pre-set period, the health management server 100 can automatically transmits health information to the home gateway server 102 whenever the user health information is updated, and the home gateway server 102 can request the health information at a time at which a pre-set condition is satisfied.

Although an indoor home network system is described for example in the above description, the present disclosure is not limited to the indoor home network system. For example, the same is also applicable to an example in which a network system for controlling devices used inside a company is implemented in the company.

Methods based on the embodiments disclosed in the claims and/or specification of the present disclosure can be implemented in hardware, software, or a combination of both.

When implemented in software, non-transient computer readable recording medium for storing one or more programs (i.e., software modules) can be provided. The one or more programs stored in the computer readable recording medium are configured for execution performed by one or more processors in an electronic device such as a portable terminal. The one or more programs include instructions for allowing the electronic device to execute the methods based on the embodiments disclosed in the claims and/or specification of the present disclosure.

The program (i.e., the software module or software) can be stored in a random access memory, a non-volatile memory including a flash memory, a Read Only Memory (ROM), an Electrically Erasable Programmable Read Only Memory (EEPROM), a magnetic disc storage device, a Compact Disc-ROM (CD-ROM), Digital Versatile Discs (DVDs) or other forms of optical storage devices, and a magnetic cassette. Alternatively, the program can be stored in a memory configured in combination of all or some of these storage media. In addition, the configured memory may be plural in number.

Further, the program can be stored in an attachable storage device capable of accessing the electronic device through a communication network such as the Internet, an Intranet, a Local Area. Network (LAN), a Wide LAN (WLAN), a Storage Area Network (SAN), or a communication network configured by combining the networks. The storage device can access the electronic device through an external port.

Furthermore, an additional storage device on the communication network can access a portable electronic device.

While the present disclosure has been particularly shown and described with reference to exemplary embodiments thereof, it will be understood by those skilled in the art that various changes in form and details may be made therein without departing from the spirit and scope of the present disclosure as defined by the appended claims.

What is claimed is:

1. A method to provide a health management service in a home gateway server configured to connect a home network with at least one home device, the method comprising:
   requesting, by the home gateway server, health information of a plurality of users including a first user to a health management server through a home gateway network;
   receiving, by the home gateway server, the health information of the plurality of users from the health management server through the home gateway network;
   generating, by the home gateway server, based on health information, environment control information for controlling the at least one home device based, the at least one home device including an indoor electronic devices that are related to everyday lives of the plurality of the users, the indoor electronic devices includes at least one of a temperature controller, a humidity controller, an illumination controller, or an air cleaner; and
   transmitting, by the home gateway server, the environment control information to the at least one home device to control the at least one home device, the environment control information including an information on at least one of a temperature, humidity, an illumination, or an air cleanness,
   wherein generating the environment control information comprises:
      analyzing patterns that are related to the everyday lives of the plurality of the users;
      determining, by the home gateway server, based on the analyzed patterns, among a plurality of places in a home, a place where the first user spends a longest time among the plurality of the users;
      determining, by the home gateway server, a home device located in the determined place among the at least one home device; and
      generating, by the home gateway server, environment control information for controlling the determined home device according to the health information of the first user.

2. The method of claim 1, further comprising:
   generating, by the home gateway server, health aid information corresponding to the health information for the plurality of users; and
   transmitting, by the home gateway server, the generated health aid information to at least one terminal, wherein the at least one terminal includes at least one of terminals corresponding to the plurality of users and a terminal corresponding to another user.

3. The method of claim 2, wherein the health aid information includes at least one of a user's illness name, a cause, a symptom, a prescription, a health condition, a cure and prevention, treatment reservation information, and food.

4. The method of claim 1, wherein the health information includes at least one of diagnosis records, prescription information, treatment reservation information, and related medical information of the plurality of users.

5. An apparatus configured to provide a health management service in a home gateway server configured to connect a home network with at least one home device, the apparatus comprising:
- a communication unit; and
- a controller configured to control to:
  - request, via the communication unit, health information of a plurality of users including a first user to a health management server through a home gateway network;
  - receive, via the communication unit, the health information of the plurality of users from the health management server through a home gateway network;
  - generate, based on the health information, environment control information for controlling the at least one home device, the at least one home device including an indoor electronic devices that are related to everyday lives of the plurality of the users, the indoor electronic devices includes at least one of a temperature controller, a humidity controller, an illumination controller, or an air cleaner;
  - transmit, via the communication unit, the environment control information to the at least one home device to control the at least one home device, the environment control information including an information on at least one of a temperature, humidity, an illumination, or an air cleanness,
  - wherein, to generate the environment control information, the controller is further configured to:
    - analyze patterns that are related to the everyday lives of the plurality of the users;
    - determine, among a plurality of places in a home, a place where the first user spends longest time among the plurality of the users;
    - determine a home device located in the determined place among at least one home device; and
    - generate environment control information for controlling the determined home device according to the health information of the first user.

6. The apparatus of claim 5, wherein:
the controller is configured to generate health aid information corresponding to the health information for the plurality of users; and
the communication unit is configured to transmit the generated health aid information to at least one terminal, and wherein the at least one terminal includes at least one of terminals corresponding to the plurality of users and a terminal corresponding to another user.

7. The apparatus of claim 6, wherein the health aid information includes at least one of a user's illness name, a cause, a symptom, a prescription, a health condition, a cure and prevention, treatment reservation information, and food.

8. The apparatus of claim 5, wherein the health information includes at least one of a diagnosis record, prescription information, treatment reservation information, and related medical information of the plurality of users.

* * * * *